United States Patent
Shabani Hendkhaleh

(10) Patent No.: US 11,779,474 B2
(45) Date of Patent: Oct. 10, 2023

(54) PARA-CYCLING KNEE JOINT

(71) Applicant: Hadi Shabani Hendkhaleh, Tehran (IR)

(72) Inventor: Hadi Shabani Hendkhaleh, Tehran (IR)

(73) Assignee: Hadi Shabani Hendkhaleh, Tehran (IR)

( * ) Notice: Subject to any disclaimer, the term of this patent is extended or adjusted under 35 U.S.C. 154(b) by 35 days.

(21) Appl. No.: 17/349,694

(22) Filed: Jun. 16, 2021

(65) Prior Publication Data
US 2022/0401234 A1    Dec. 22, 2022

(51) Int. Cl.
*A61F 2/64* (2006.01)
*A61F 2/80* (2006.01)
*A61F 2/50* (2006.01)

(52) U.S. Cl.
CPC .............. *A61F 2/64* (2013.01); *A61F 2/80* (2013.01); *A61F 2002/5069* (2013.01); *A61F 2310/00023* (2013.01); *A61F 2310/00047* (2013.01)

(58) Field of Classification Search
CPC ...... A61F 2/64; A61F 2/80; A61F 2002/5069; A61F 2002/00023; A61F 2002/00047
See application file for complete search history.

(56) References Cited

U.S. PATENT DOCUMENTS

| | | | | |
|---|---|---|---|---|
| 1,690,194 | A * | 11/1928 | Girton | A61F 2/64 623/39 |
| 8,313,534 | B1 * | 11/2012 | Chen | A61F 2/644 623/43 |
| 2005/0021153 | A1 * | 1/2005 | Curtis | A61F 2/76 623/38 |
| 2006/0069449 | A1 * | 3/2006 | Bisbee, III | A61F 2/64 623/46 |
| 2008/0071387 | A1 * | 3/2008 | Olafsson | A61F 2/70 188/297 |
| 2011/0093090 | A1 * | 4/2011 | Olafsson | A61F 2/78 623/38 |
| 2012/0310372 | A1 * | 12/2012 | Omarsson | A61F 2/644 623/39 |

(Continued)

*Primary Examiner* — Jerrah Edwards
*Assistant Examiner* — Maximilian Tobias Spencer
(74) *Attorney, Agent, or Firm* — Kilpatrick Townsend & Stockton LLP

(57) ABSTRACT

Disclosed is a para-bi-cycling knee joint prosthesis for interconnecting a prosthetic lower leg and a prosthetic thigh, the knee joint prosthesis including an upper body portion configured to support a socket adapter, for connection with a prosthetic thigh; a lower body portion extending from the upper body portion and configured to connect with a prosthetic lower leg; a pair of ball bearings mounted on ends of a pivot shaft, the pivot shaft forming un upper part of the lower body portion, the upper body portion having left and right upper body portions, each configured to receive the external surface of one of the bearings, thus enabling rotation between the upper and lower body portions; the rotation allowing for flexion between the upper and the lower body portions of at least 140 degrees; and the upper body portion having an extended surface configured to engage a complementarily-shaped surface of the lower body portion, to prevent the backward rotation of the knee joint.

17 Claims, 6 Drawing Sheets

(56) References Cited

U.S. PATENT DOCUMENTS

| | | | |
|---|---|---|---|
| 2015/0265434 A1* | 9/2015 | Hurley | A61F 2/5044 623/33 |
| 2015/0313729 A1* | 11/2015 | Williams | A61F 2/64 623/33 |
| 2017/0281370 A1* | 10/2017 | Duger | A61F 2/64 |
| 2018/0289511 A1* | 10/2018 | Fairley | A61F 2/64 |
| 2020/0038203 A1* | 2/2020 | Piller | A61F 2/582 |
| 2020/0146833 A1* | 5/2020 | Johnson | A61F 2/64 |

* cited by examiner

PARA-CYCLING KNEE JOINT

FIELD OF INVENTION

The present invention relates to prosthesis devices and, more particularly, it is directed to an above-the-knee prosthesis for use when riding a bicycle.

BACKGROUND OF THE INVENTION

There are many in the world who for various reasons have lost a limb or portion thereof. Due to complications that will persists beyond amputation, routine tasks and life of an amputee will not be the same as before the loss of limb.

Loss of limb can be caused by natural phenomenon, or industrial accidents, and sometimes as a result of medical procedures for the removal of tumors or cancer. In either case, a team pf physicians will consider best practices before deciding on amputation.

An amputation can be defined as removal of a limb or outgrowth of the body. A decision to amputate is often made when an injured limb cannot be recovered to function after disease or trauma. An amputation is also a life-saving operation when no other choices are available and thus it should not be considered as a failed treatment. Surgical amputation is one of the oldest surgical procedures that has been practiced by surgeons for decades. In the somewhat current times, the development of prosthetic design and specific rehabilitation programs for people with limb loss was intensified after World War II.

A lower limb amputation (LLA) can be categorized into a major or minor amputation. A major amputation is performed proximal to the ankle joint. Meanwhile, a minor amputation is one performed distal to the ankle joint. Transfemoral amputation, knee disarticulation, and transtibial amputations are three most common levels of amputation.

In the case of a transfemoral amputation, an amputee is forced to used other muscles so as to then be able to mimic the biomechanical movement of the natural knee joint.

Many prosthetic knee joints are known. Several suppliers are even offering advanced, sensor-enabled and microprocessor-controlled devices. However, such known devices are designed for general, daily routine activities. It is also known that people with a transfemoral amputation would require specialized use and athletic use prosthesis devices when engaged in specialized or athletic activities, and not their general daily routine activities.

Amongst the prosthetic knee joints that may be used by transfemoral amputees for bicycle riding are rare samples that are custom developed for para-Olympics teams and events that are offered by some suppliers. Such highly specialized and unique devices cost well beyond the means of many transfemoral amputees who would like to enjoy the benefits of bicycle riding.

One of the properties of a knee joint prosthesis that can be used for bicycle riding is the requirement for a high flexion angle; e.g., of at least 130 Degrees. In a knee joint, the two major movements of the knee are flexion and extension; flexion being the bending the knee away from a straight leg; and extension being the movement to extend the leg back toward being straight. However the mere having of such a range for flexion does not render a prosthesis knee suitable for bicycle riding, since even modern hydraulic or even pneumatic-assisted prosthetic knee joints will tend to overheat from the repetitive pedaling and the internal friction of the moving parts during the repetitive cyclic motion. So, merely having a high range for flexion does not necessarily render a knee prosthesis suitable for bicycle riding. The requirement for high flexion during bicycle riding causes premature wear in such commercially-available and high value prosthetic knee joints, rendering their useful life for bicycling far less than adequate, and considering their relative high costs, rendering them unpractical economically for bicycle riding.

There remains a need for a high flexion knee prosthesis that does not suffer from the above shortcoming, and which is readily suitable for bicycle riding.

BRIEF SUMMARY OF THE INVENTION

The present invention provides an improved knee prosthesis that is usable for riding a bicycle. The prosthesis knee joint is extremely durable and yet made of very few parts and is easily maintainable and repairable. The way in which such a prosthesis is able to impact people's mobility is tremendous in the same way as wheeled cycle is advantageous over foot traffic, here magnified due the amputation.

Embodiments of the present invention allow for persons with a transfemoral amputation to enjoy riding a bicycle by using the lower limb prosthesis for an above-knee amputee having the improved knee joint according to the embodiments of the present invention, which is especially configured for bicycle riding. The knee joint in accordance with the embodiments of the present invention has many advantageous features. These features include an angle of flexion higher than 130 degrees, and improved heat transfer from the prosthesis, which is achieved by use of ball-bearings to allow for a nearly friction free knee joint.

Other advantages of this novel knee joint include the low cost of the device and the relative ease with which the knee joint prosthesis may be made using a minimal number of parts that are easy to manufacture and even easier to assemble or maintain. Such advantageous features will enable a strong and durable knee joint designed for near-friction-free use for bicycle riding.

In one aspect, the present invention is directed towards a para-bi-cycling knee joint prosthesis for interconnecting a prosthetic lower leg and a prosthetic thigh, the knee joint prosthesis including an upper body portion configured to support a socket adapter, for connection with a prosthetic thigh; a lower body portion extending from the upper body portion and configured to connect with a prosthetic lower leg; a pair of ball bearings mounted on ends of a pivot shaft, the pivot shaft forming un upper part of the lower body portion, the upper body portion having left and right upper body portions, each configured to receive the external surface of one of the bearings, thus enabling rotation between the upper and lower body portions; the rotation allowing for flexion between the upper and the lower body portions of at least 140 degrees; and the upper body portion having an extended surface configured to engage a complementarily-shaped surface of the lower body portion, to prevent the backward rotation of the knee joint.

In one aspect, the socket adapter can be a male pyramid adapter, where the male pyramid adapter is connected with the right and the left upper body portions using hand-turnable fasteners; thus connecting the left upper body portion with the right upper body portion with one-another at the socket adapter.

In another aspect, the socket adapter can be a female pyramid adapter, where the female pyramid adapter is connected with the right and the left upper body portions using hand-turnable fastener; thus connecting the left upper body portion with the right upper body portion with one-another at the socket adapter.

In another aspect, the socket adapter is a 4-prong socket adapter, where the socket adapter is connected with the right and the left upper body portions using hand-turnable fastener; thus connecting the left upper body portion with the right upper body portion with one-another at the socket adapter.

In another aspect, the socket adapter is a four-hole adapter, where the four hole adapter is connected with the right and the left upper body portions using hand-turnable fastener; thus connecting the left upper body portion with the right upper body portion with one-another at the socket adapter.

In one aspect, the upper body portion is made using a titanium or an aluminum alloy.

In another aspect, the lower body portion is made from an aluminum or titanium alloy.

In another aspect, the left and right upper body portions are dimensioned to press-fit receive the bearings.

In another aspect, the left and right upper body portions each include grooves to receive retaining rings, and also include left and right retaining rings dimensioned to fit within the grooves, so as to positively secure the bearings within the upper body portion.

In another aspect, the lower body portion has a hollow central connecting tube for receiving a prosthetic lower leg.

In another aspect, the hollow central connecting tube is made from an aluminum alloy.

In another aspect, the para-bi-cycling knee joint prosthesis for interconnecting a prosthetic lower leg and a prosthetic thigh also includes a cosmetic finish for the lower body portion.

In another aspect, the upper body portion connects with the lower body portion by the use hand tightened fasteners.

In another aspect, the upper body portion is connected with the lower body portion via shaft held by the upper body being engaged by the bearings held by the lower body portion.

In another aspect, the left and right upper body portions, are configured to form a unitary body at the socket adapter by way of a press-fit.

In another aspect, the lower body portion includes a connecting hollow tube at a distal end thereof.

In another aspect, the para-bi-cycling knee joint prosthesis for interconnecting a prosthetic lower leg and a prosthetic thigh also includes a silicon cover configured to fit over the prosthesis once assembled and before deployment by the amputee.

The construction and operation of the embodiments of the prosthesis device in accordance with the embodiments of the present invention may be best understood by reference to the following description taken in conjunction with the accompanying drawings.

DETAILED DESCRIPTION OF THE INVENTION

Figure 1:
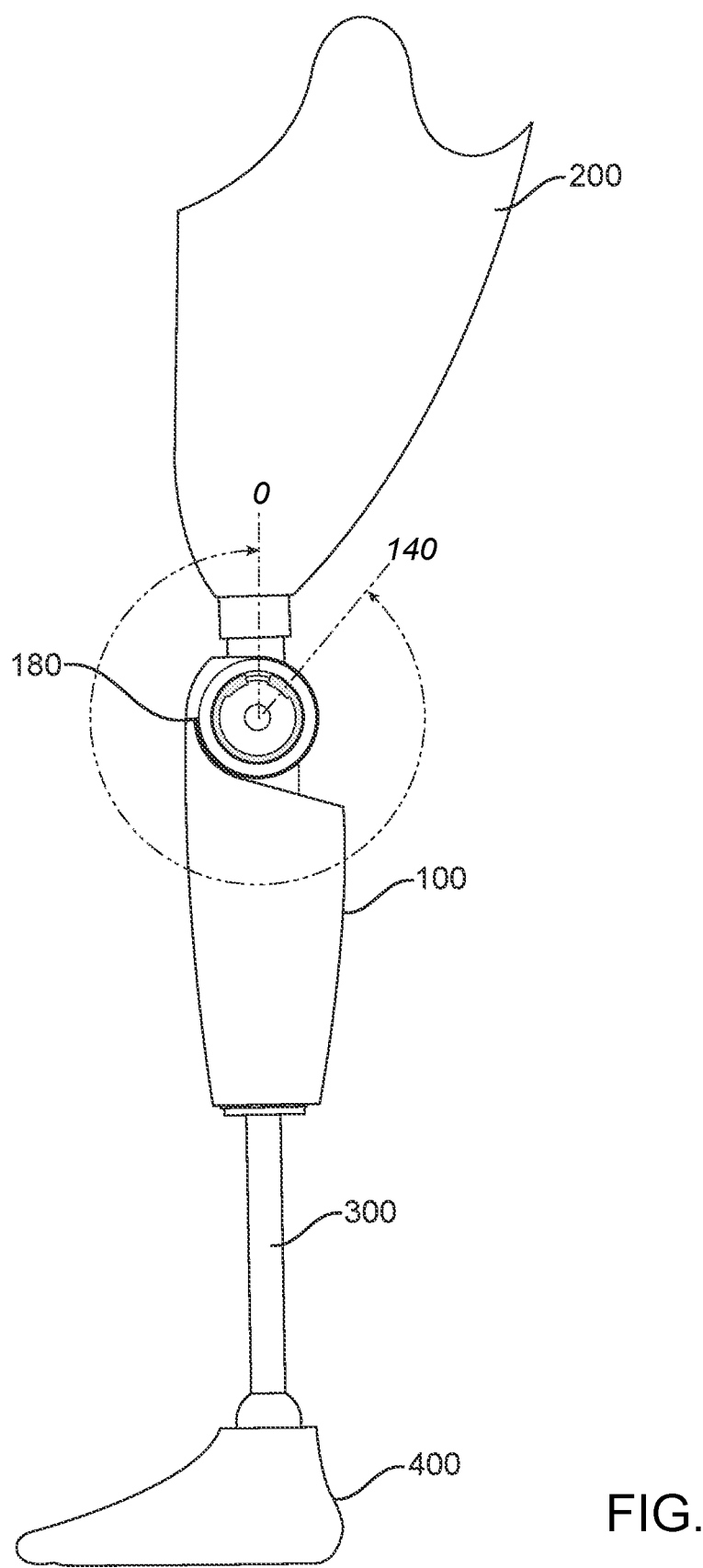
FIG. 1 shows the lower limb prosthesis for an above-knee amputee, according to the embodiments of the present invention.

People with a transfemoral amputation use an above-the-knee prosthesis to compensate for their loss of mobility. Such an above-the-knee prosthesis is made from a socket portion, a knee portion, a pylon and shank portion and a foot portion. Sockets are custom made for each person.

The knee join is typically connected at its top or proximal end with an adapter with the socket and at its lower or distal end with another connector or adapter to connect the knee with a pylon or shank.

Considering the above-described shortcomings of the known prosthesis knee joints for use for bicycle riding, the knee joint in accordance with the embodiments of the present invention is uniquely focused for use for bicycle riding. The para-bi-cycling knee joint prosthesis in accordance with the embodiments of the present invention, allows for flexion of at least 140 degrees, also while requiring the least energy for the pedaling effort. The technical features of this knee prosthesis are such that repeated and ongoing pedaling does not result in overheating or muscle fatigue. And considering the heavy load due to the repeated cycling load, the design of this knee prosthesis enables the prolonged use of the knee prosthesis.

Referring to drawings and more particularly to FIG. 1-5, there is shown a prosthesis 100, according to the embodiments of the present invention. This knee device 100 comprises a single pivot between the thigh socket 200 and shank 300, seen in FIG. 1. The knee 100 also includes a locking feature 180 to help keep the leg straight when standing and to prevent backward rotation beyond a straight leg, best seen in FIG. 5.

In accordance with the embodiments of the present invention, the use of aluminum and/or titanium alloys in the construction of the body of the prosthesis allow for effective transfer of heat generated during the repeated pedaling motion and which prevent the overheating of the device. The upper 102 or lower body 104, 140 portions may be made of titanium alloys or more readily available aluminum alloys. Furthermore, the use of ball bearings in the flexion pivot cause the least friction while traveling through the range of the flexion.

These features enable the design of prosthesis knee joint to be suitable for bicycle riding, and require the least expenditure of energy by the user of the device, which itself play an important role in improvements in athletic ability and improved mobility for the user of the device.

As is seen in drawings, the prosthesis knee in accordance with the embodiments of the present invention, allows for flexion of at least 140 degrees.

As is seen in the drawings; the para-cycling knee joint prosthesis 100 connects a prosthetic lower leg 300 and foot 400 with and a prosthetic thigh 200. The device includes pair of bearings 106A/106B. The bearings 106A/106B are mounted to shaft 114 fitted inside the upper portion of the lower body 104. Body 104 includes the upper portion to receive the shaft 114 and bearings 106A/106B. Extending from the lower body 104 is hollow shaft 160 which terminates at its proximal end at the pylon clamp screw 150. The proximal end of the shaft 160 is dimensioned to receive a pylon or shank portion 300. Clamp screw 150 is configured for being hand tightened to securely hold the shank 300 in place with respect to the knee joint 100. Other suitable adapters or connectors may also be used as alternatives to the clamp screws 150.

Once the lower body is assembled, upper body portions 102A/102B are press fit over the bearings 106A/106B respectively. At this partial assembly stage the two bearings may pivot with respect to one-another. Next, the upper socket adapter 110 is connected with the right and left upper body portions 102A/102B to form a unitary upper body portion. Next, retaining rings 109A/109B are placed in the grooves formed to receive them to securely hold them in place within the upper body.

Figure 6:
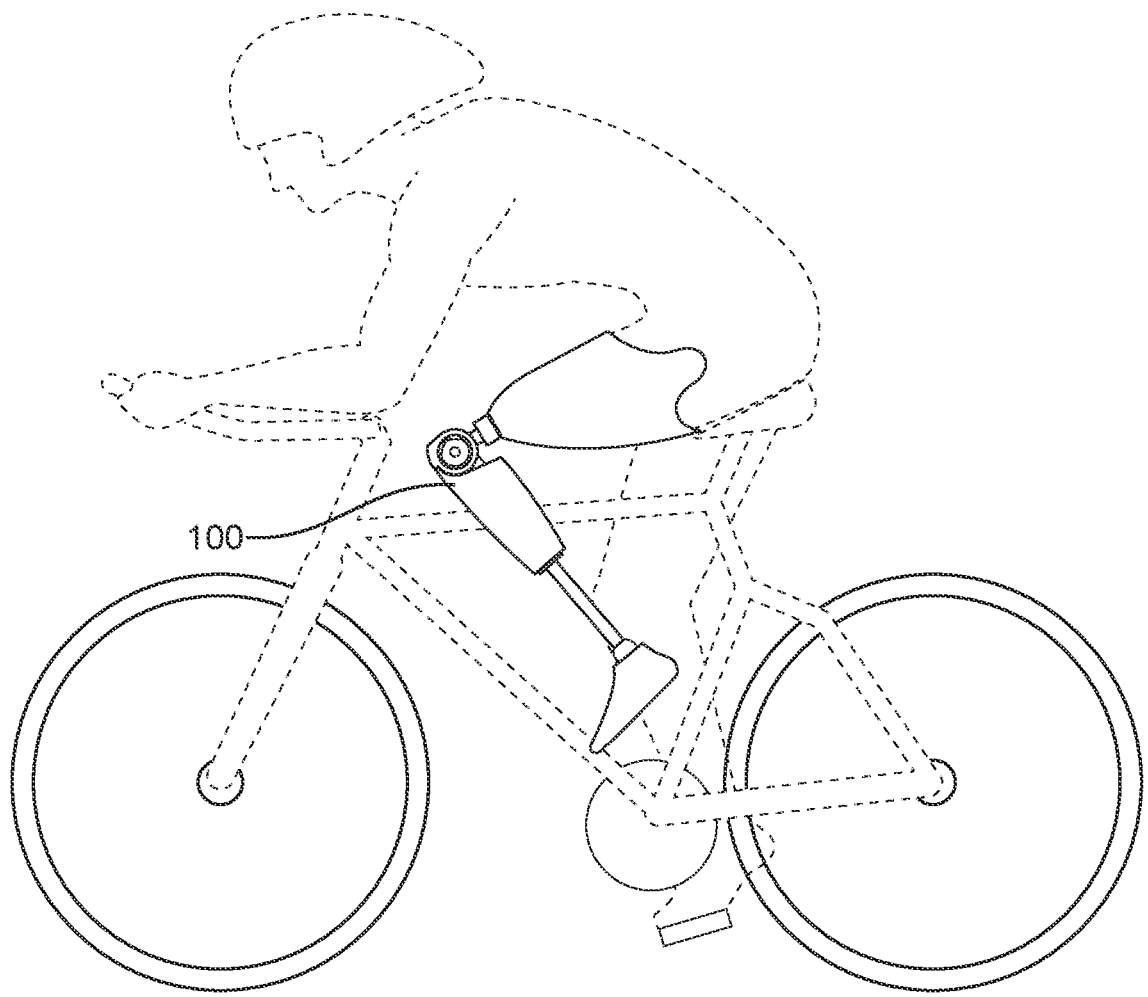
FIG. 6 shows the knee prosthesis flexed while riding a bicycle.

The use of ball bearings allows for very high flexion and the overall shape of the lower portion and the socket allow for flexion of at least 140 degrees (FIG. 1), solely limited by interference when the knee is flexed as seen in FIG. 6.

The upper socket adapter 110 may be a male pyramid adapter, a female socket adapter, a 4 prong adapter or a 4 hole adapter, or another suitable adapter for connecting with the socket.

One possible order of assembly for the knee prosthesis may be as follows: placing bearings on connecting shaft end configured to receive the bearings; placing right and left upper body socket portions over the bearings; placing right and left retaining rings to secure the bearings within the body socket portions from lateral shift; connecting the joint/socket adapter with the right and left upper body portions using fasteners; connecting the shank/shin with the pylon clamp screw at end of hollow shaft; placing a silicon cover over lower portion, hollow shaft; and connecting the joint/socket adapter with socket. The silicon cover is configured to prevent or minimize accidental damage to amputees skin. The silicon cover may wrap around or over or surround the lower body portion 140.

The fasteners 112 may be allen-type fasteners, or other suitable or readily available fasteners to allow for ease of manufacturing maintainability.

The para-bi-cycling knee joint prosthesis for interconnecting a prosthetic lower leg and a prosthetic thigh offers many advantages for the above the knee amputee. As mentioned above, the use of titanium or aluminum alloys used for the upper body portions 102A/B and lower portion 104, 140 allow for effective transfer of heat away from the pivoting bearings to prevent the knee from overheating. The press fit and the resulting close contact between the upper body and the bearing casings enable the effective heat transfer.

Furthermore, the use of titanium or aluminum alloys in the upper body 102A/B of the knee joint, in combination with the minimal number of components renders the overall weight to be low so as to enable cycling without undue fatigue. Lower body portion 140 can be made of titanium or aluminum alloys.

The use of ball bearings in the upper portion of the prosthesis, which itself is made of titanium or aluminum alloys allows for the transfer of heat out of the joint and away from the device and the wearer. The use of ball bearings results in very little friction during the flexion, and the light force required to push the light load of the ball-bearings renders the pedaling very easy, making it suitable even for those who have recently had their above the knee amputation.

Figure 2:
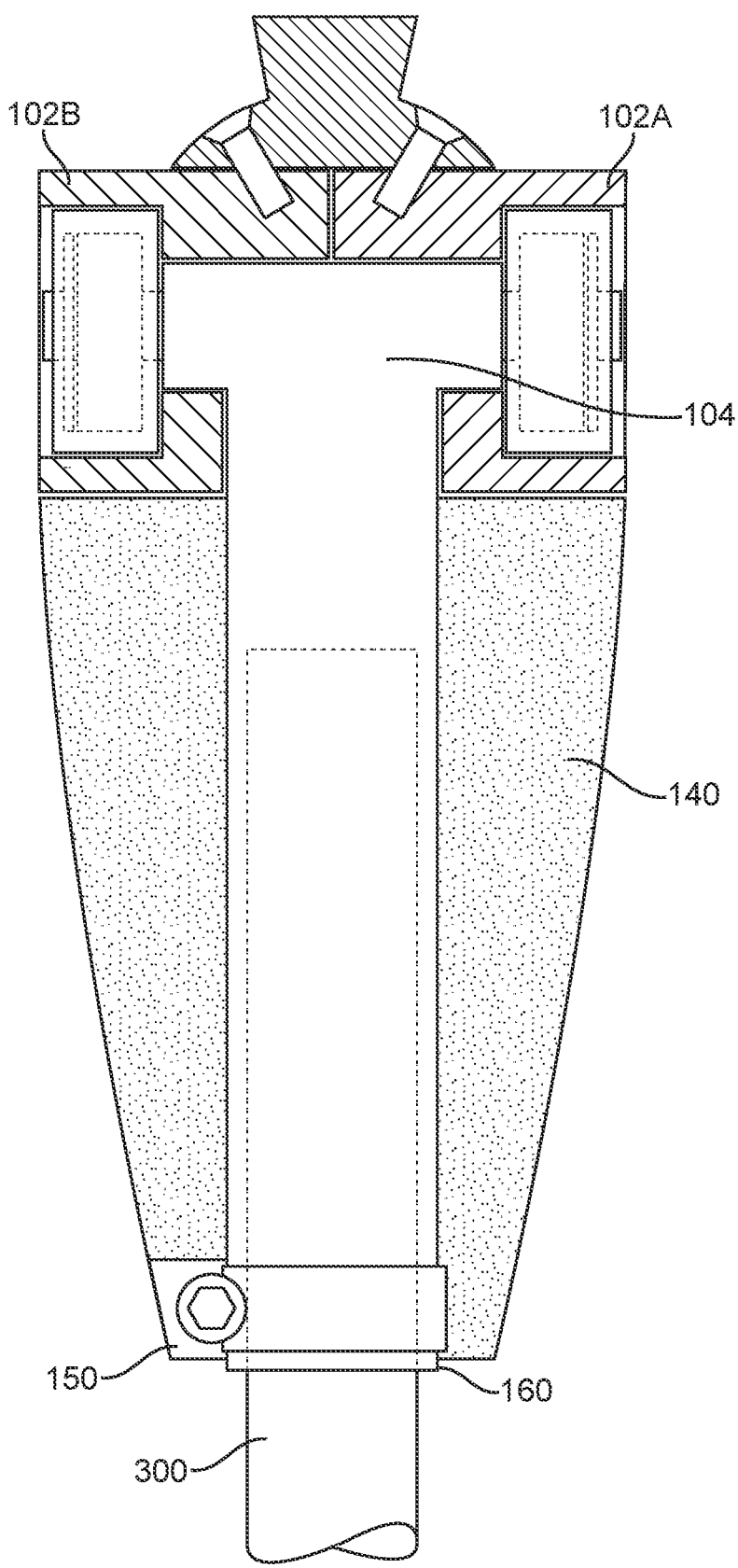
FIG. 2 is a partial x-sectional view of the knee prosthesis of FIG. 1 where the bearings and pivot shaft are partially hidden.
Figure 3:
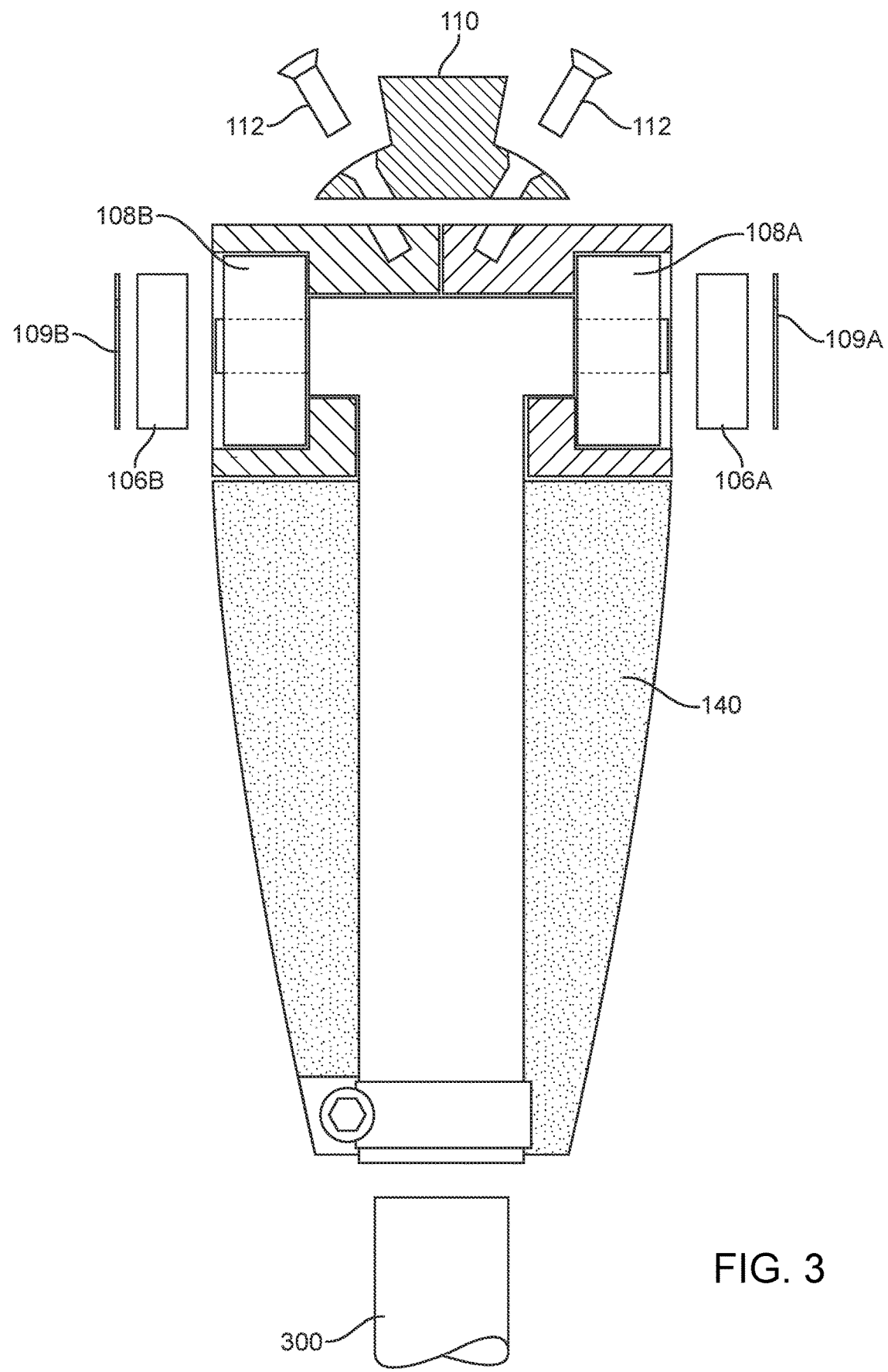
FIG. 3 is an exploded assembly view of the knee prosthesis of FIG. 2.
Figure 4:
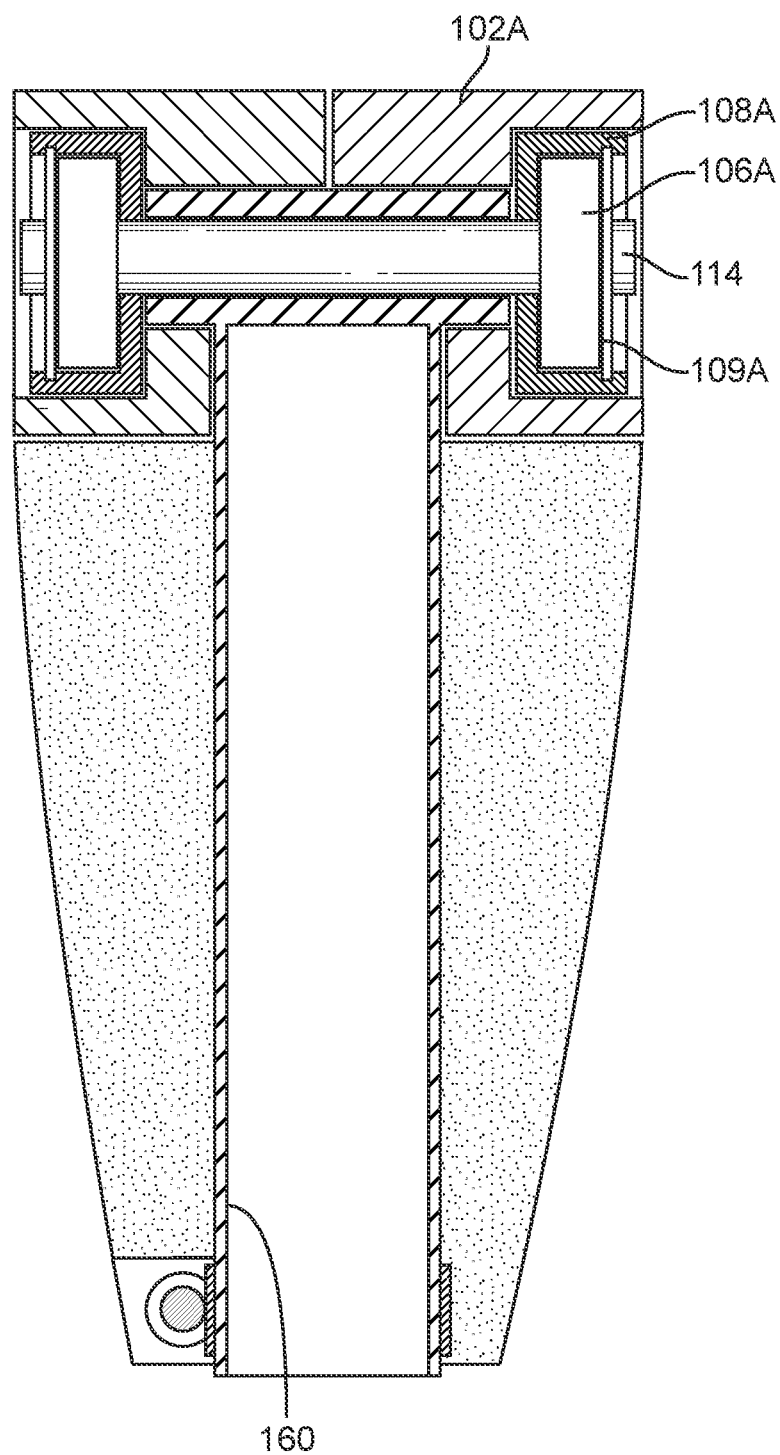
FIG. 4 is a sectional view of FIG. 3, shown without the upper socket adapter.
Figure 5:
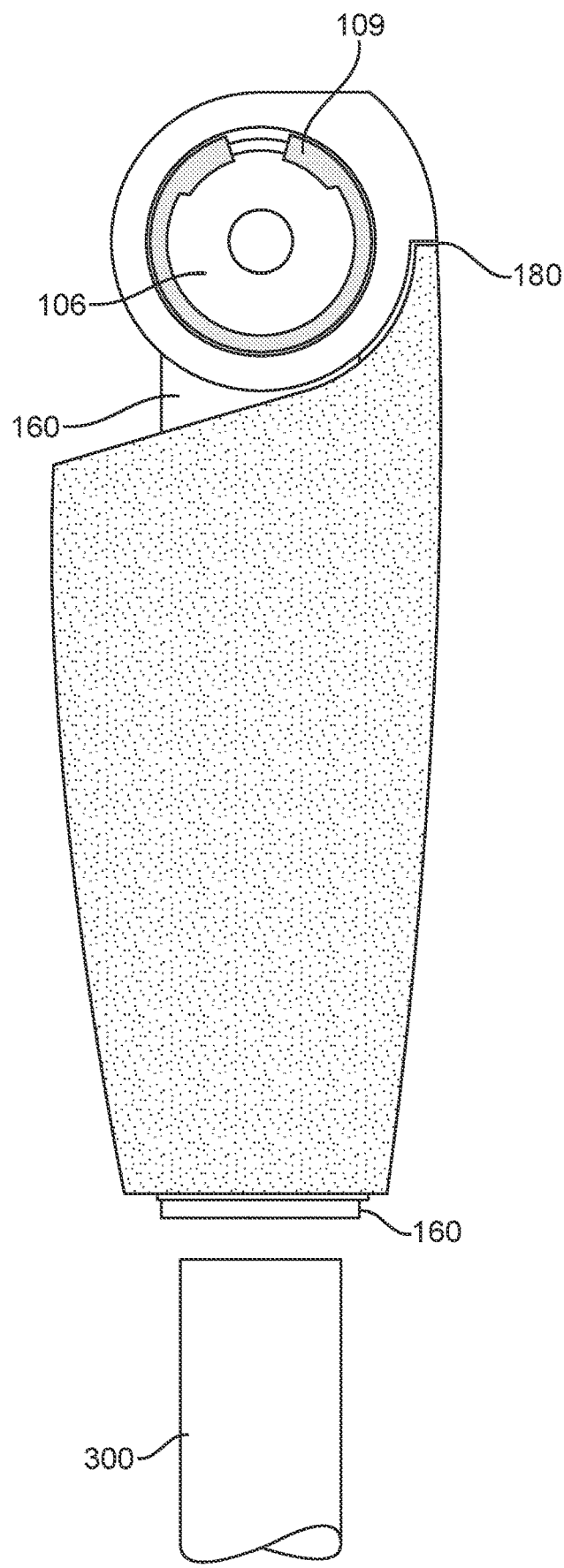
FIG. 5 is a side view of the knee prosthesis of FIG. 4, also showing the shin/shank piece ready to be received by the hollow tube.

Referring to FIGS. 1-3, pylon coupling or clamp screw 150 and the hollow shaft 160 allow for wide range of variability for the shin or shank length for the wearer. This allows for the device to be easily adjusted for the same person on different occasions to match a desired length or different person entirely.

The para-cycling knee prosthesis in accordance with the embodiments of the present invention, by being elegantly simple in design, allows for the device to be manufactured at a very low cost, rendering the device well within the economic reach of above-knee amputees. Likewise, the device is very easy to completely disassemble, maintain and/or repair.

The above-described features and advantages not seen on other knee prosthesis joints allow for the device in accordance with the present invention to be extremely adaptable and conformable for above-knee amputee bicycle riders.

There has thus been described an improved para-bicycling knee joint prosthesis for interconnecting a prosthetic lower leg and a prosthetic thigh. The knee joint allows for very high flexion, minimal friction and high durability for bicycle riding, while having a lock feature to prevent the backward extension of the knee prosthesis. While the prosthesis has been described above, accordingly, various modifications of the prosthesis will occur to persons skilled in the art without involving any departure from the spirit and scope of the invention as set forth in the appended claims.

What is claimed is:

1. A para-bi-cycling knee joint prosthesis adapted for interconnecting a prosthetic lower leg and a prosthetic thigh, said knee joint prosthesis comprising:
   an upper body portion configured to support a socket adapter for connection with a prosthetic thigh, said upper body portion comprising a left upper body portion and a right upper body portion separable from the left upper body portion, each of the left and right portions comprises a recess;
   a lower body portion comprising a longitudinally extending body with a proximal end and a distal end, a shaft receiving portion having a T-shape projecting from the proximal end and a hollow central connecting tube extending from the shaft receiving portion toward the distal end for receiving a prosthetic lower leg, wherein the left upper body portion covers a left side portion of the T-shape and a left side gap between the T-shape and the proximal end, and the right upper body portion covers the right side portion of the T-shape and a right side gap between the T-shape and the proximal end;
   a pivot shaft disposed in the shaft receiving portion of the lower body portion and extending along the left and right upper body portions; and
   a pair of ball bearings mounted on ends of the pivot shaft such that the pivot shaft passes through said bearings, wherein each of said bearings are disposed within the recess of the left and right upper body portions, respectively, thus enabling rotation between said upper and lower body portions; said rotation allowing for flexion between the upper and the lower body portions of at least 140 degrees, wherein external surface of said bearing are in direct contact with an inner surface of the recess to facilitate heat dissipation from said bearing to said upper body portion; and
   said upper body portion comprising an extended surface configured to engage a complementarily shaped surface of the lower body portion to prevent the backward rotation of the knee joint.

2. The device of claim 1, wherein said socket adapter is a male pyramid adapter, said male pyramid adapter connected with the right and the left upper body portions using hand-turnable fastener; thus connecting the left with the right with one-another at the socket adapter.

3. The device of claim 1, wherein said socket adapter is a female pyramid adapter, said female pyramid adapter connected with the right and the left upper body portions using hand-turnable fastener; thus connecting the left with the right with one-another at the socket adapter.

4. The device of claim 1, wherein said socket adapter is a 4-prong socket adapter, said socket adapter connected with the right and the left upper body portions using hand-turnable fastener.

5. The device of claim 1, wherein said socket adapter is a four-hole adapter, said four hole adapter connected with the right and the left upper body portions using hand-turnable fastener; thus connecting the left with the right with one-another at the socket adapter.

6. The device of claim 1, wherein said upper body portion is made using a titanium alloy.

7. The device of claim 1, wherein said lower body portion is made from an aluminum alloy.

8. The device of claim 1, where the left and right upper body portions are dimensioned to press-fit receive the bearings.

9. The device of claim 1, wherein the left and right upper body portions each include grooves to receive retaining rings, and further comprising left and right retaining rings dimensioned to fit within said grooves, so as to positively secure the bearings within the upper body portion.

10. The device of claim 1, wherein said hollow central connecting tube is made from an aluminum alloy.

11. The device of claim 1, further comprising a cosmetic finish for the lower body portion.

12. The device of claim 1 where the upper body portion connects with the lower body portion with hand tightened fasteners.

13. The device of claim 1, wherein the upper body portion is connected with the lower body portion via shaft held by the upper body being engaged by the bearings held by the lower body portion.

14. The device of claim 1, wherein the left and right upper body portions, are configured to form a unitary body by way of a press-fit.

15. The device of claim 1, wherein the lower body portion comprises a connecting hollow tube at a distal end thereof.

16. The device of claim 1, further comprising a silicon cover configured to fit over the lower limb prosthesis for an above-knee amputee once assembled and before deployment by the amputee.

17. A para-bi-cycling knee joint prosthesis adapted for interconnecting a prosthetic lower leg and a prosthetic thigh, said knee joint prosthesis consisting of:

an upper body portion configured to support a socket adapter, for connection with a prosthetic thigh;

a lower body portion extending from said upper body portion, and configured to connect with a prosthetic lower leg;

a pair of ball bearings mounted on ends of a pivot shaft, said pivot shaft forming un upper part of said lower body portion, said upper body portion comprising left and right upper body portions, each configured to receive the external surface of said bearings, thus enabling rotation between said upper and lower body portions; said rotation allowing for flexion between the upper and the lower body portions of at least 140 degrees; and said upper body portion comprising an extended surface configured to engage a complementarily shaped surface of the lower body portion to prevent the backward rotation of the knee joint.

* * * * *